(12) United States Patent
Farkas et al.

(10) Patent No.: US 6,458,371 B1
(45) Date of Patent: Oct. 1, 2002

(54) COSMETIC COMPOSITION AND A METHOD FOR THE PREVENTION AND/OR REDUCTION OF THE PHOTOAGING PROCESSES OF THE SKIN

(75) Inventors: Bea Farkas, Szeged; Peter Literati Nagy; Agnes Vadasz, both of Budapest; Laszlo Vigh, Szeged, all of (HU)

(73) Assignee: Medgene, Limited, Tortola (VG)

( * ) Notice: Subject to any disclaimer, the term of this patent is extended or adjusted under 35 U.S.C. 154(b) by 0 days.

(21) Appl. No.: 09/205,281

(22) Filed: Dec. 4, 1998

Related U.S. Application Data

(63) Continuation-in-part of application No. 08/771,410, filed on Dec. 20, 1996, now abandoned.

(30) Foreign Application Priority Data

Dec. 22, 1995 (HU) .............................................. 9503728

(51) Int. Cl.[7] .......................... A61K 6/00; A01N 25/00
(52) U.S. Cl. ...................... 424/401; 514/844; 514/845; 514/846
(58) Field of Search .......................... 424/401; 514/844, 514/845, 846

(56) References Cited

U.S. PATENT DOCUMENTS

| | | | | | |
|---|---|---|---|---|---|
| 4,187,220 | A | * | 2/1980 | Takacs et al. | 540/483 |
| 4,308,399 | A | * | 12/1981 | Takacs et al. | 564/257 |
| 5,239,077 | A | * | 8/1993 | Bertok et al. | 546/193 |
| 5,278,309 | A | * | 1/1994 | Bertok et al. | 546/193 |
| 5,296,606 | A | | 3/1994 | Nagy et al. | 546/193 |
| 5,571,794 | A | * | 11/1996 | Frome | 514/23 |

OTHER PUBLICATIONS

Kurihara et al., *Chemical Abstracts Plus*, vol. 94, #30304, 1981.
Takacs et al., *Chemical Abstracts Plus*, vol. 89, #6123, 1978.
Lion, *World Patent Index*, 83–720852, 1983.
Bissett et al., *Chemical Abstracts*, vol. 112, #223133, 1990.

* cited by examiner

*Primary Examiner*—Michael G. Hartley
*Assistant Examiner*—Michael A. Willis
(74) *Attorney, Agent, or Firm*—Birch Stewart Kolasch & Birch LLP

(57) ABSTRACT

A novel cosmetic composition comprising a known hydroximic acid derivative as the active ingredient, and conventional carriers of the cosmetic composition are disclosed. The cosmetic composition of the invention is suitable for the prevention and/or reduction of the photoaging processes of the skin exposed to UV radiation.

18 Claims, No Drawings

COSMETIC COMPOSITION AND A METHOD FOR THE PREVENTION AND/OR REDUCTION OF THE PHOTOAGING PROCESSES OF THE SKIN

This application is a continuation-in-part of application Ser. No. 08/771,440 filed on Dec. 20, 1996, now abandoned, the entire contents of which are hereby incorporated by reference.

FIELD OF THE INVENTION

The invention refers to a cosmetic composition and a method for the prevention and/or reduction of the photoaging processes of the skin.

BACKGROUND OF THE INVENTION

Exposure of human skin to sunlight has several known unpleasant effects such as sunburn and carcinogenesis. Due to the ultraviolet radiation in sunlight, free radicals (e.g., hydroxy radicals or nascent oxygen) form in the skin. Such free radicals can injure the DNA of skin cells and contribute to photoaging of the skin.

Photoaging includes changes attributable to chronic sun exposure and results in dry skin, wrinkling, laxity or even a variety of benign neoplasms.

Free radicals having a powerful oxidizing effect can injure the membrane of cells by oxidizing the unsaturated fatty acid components of the membrane (peroxidization of lipids). Also, reactive aldehydes are formed during the oxidization. In the injury of the membrane, increased intake of calcium leads to cell death, and pathological processes are started due to the presence of the reactive aldehydes:

injury of DNA, resulting in mutation in both the cell nucleus and mitochondria;

changes in the properties of the interstitial proteins (i.e., elastin) owing to the formation of crosslinks.

It is known that the elastic structures of collagen proteins and elastin contain a lot of water. It is characteristic of the interstitial proteins that they are rich in lysine. The reactive aldehydes such as malondialdehyde result in condensation reactions with the protein side chains containing amino groups to yield crosslinks. Thus, the originally elastic structure of the skin becomes rigid and hydrophobic. During the above process, at first lipofuscin ceroids, then age pigments are formed.

The natural protective mechanisms against ultraviolet radiation include bronzing due to the formation of melanin, DNA repair mechanisms, etc. Deficiency of a protective mechanism such as DNA repair, with consequent loss of the correction of the DNA injuries caused by ultraviolet radiation leads to early photoaging of the skin. Xeroderma pigmentosum is a disease characterized by deficiency of DNA repair that can be accompanied by the development of a malignant tumor. Sunburn spots caused by bronzing in early childhood are photodamage that heals, leaving an extended scar that can result in spinocellular carcinoma or even in various malignant tumors (e.g., melanoma, ceratoacanthoma, basalioma, sarcoma).

Suntan compositions such as oils, creams or lotions containing UV light protective agents, if used, can eliminate sunburn. However, side effects like allergic contact dermatitis, photoallergic contact dermatitis, irritative dermatitis and photosensitivity are often experienced, especially on repeated use of the suntan compositions comprising a high amount of a UV light protective agent that either reflects or absorbs UV light. A further deficiency of the known suntan compositions is that they must be used before the UV exposure of the skin. After sunburn of an unprotected skin surface, the photodamage cannot be reduced by subsequent treatment of the exposed skin with the suntan composition.

Thus, there is an existing demand for a cosmetic composition that is efficient in both the prevention and the reduction of photoaging.

The hydroximic acid derivatives of Formula I below are known from Hungarian Patent No. 177 578 and its equivalent U.S. Pat. No. 4,308,399. The known compounds are suitable for the treatment of diabetic angiopathy.

Hungarian Patent No. 207 988 and its equivalent European Patent No. 417 210 and U.S. Pat. No. 5,296,606 describe related compounds, namely, hydroximic acid halides having a selective beta-blocking effect, thus being suitable for the treatment of diabetic angiopathy.

Hungarian Patent Application No. 2385/92 published under No. T/66350 describes further hydroximic acid derivatives. These known compounds can be used in the treatment of vascular deformations, mainly in the therapy of diabetes mellitus.

Only pharmaceutical compositions, for internal use, containing the hydroximic acid derivatives of Formula I have been described in the above literature.

Use of hydroximic acid compounds of Formula I for prevention or treatment of skin conditions is novel.

DESCRIPTION OF THE INVENTION

The invention refers to a cosmetic composition comprising a hydroximic acid derivative of the formula

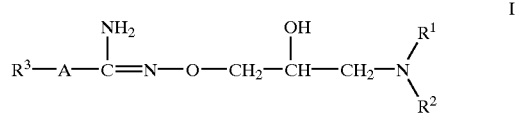

wherein $R^1$ is a hydrogen atom or a $C_{1-5}$ alkyl group;

$R^2$ is a hydrogen atom or a $C_{1-5}$ alkyl group, a $C_{5-7}$ cycloalkyl group or a phenyl group, optionally substituted by a hydroxy group; or $R^1$ and $R^2$ together with the nitrogen atom to which they are attached form a 5 to 8 membered ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of the formula

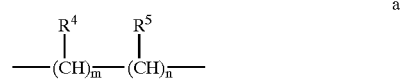

wherein $R^4$ is a hydrogen atom or a phenyl group;

$R^5$ is a hydrogen atom or a phenyl group;

m has a value of 0, 1 or 2; and n has a value of 0, 1 or 2; or a physiologically acceptable acid addition salt thereof as the active ingredient.

The aim of the invention is to provide a cosmetic composition and a method for the prevention and/or reduction of the photoaging processes of the skin.

"Prevention of the photoaging processes of the skin" means that practically no photodamage is experienced when, after treatment of the skin with a composition of the invention, the skin is exposed to UV light radiation of the usual intensity during sun-bathing.

"Reduction of the photoaging processes of the skin" means that a significantly lower rate of photodamage is observed on a skin surface treated with the composition of the invention after UV light exposure of the usual intensity during sun-bathing than on an untreated skin surface exposed to UV light of the same intensity.

It was found that the above aim is fulfilled by a cosmetic composition comprising a hydroximic acid derivative of the Formula I or a physiologically acceptable acid addition salt thereof as the active ingredient.

The term "composition" as used herein means a composition that is suitable for topical treatment and which is applied to the skin surface in a conventional manner.

The composition of the invention comprises a hydroximic acid derivative of Formula I or a physiologically acceptable acid addition salt thereof as the active ingredient in admixture with one or more conventional carriers of typical cosmetic compositions.

A $C_{1-5}$ alkyl group is, for example, a methyl, ethyl, n-propyl, isopropyl, n-butyl or n-pentyl group, preferably a methyl or an ethyl group.

A $C_{5-7}$ cycloalkyl group is a cyclopentyl, cyclohexyl, or cycloheptyl group, preferably a cyclopentyl or cyclohexyl group.

A 5 to 8 membered ring containing one or more heteroatoms can be, for example, a pyrrole, pyrazole, imidazole, oxazole, thiazole, pyridine, pyridazine, pyrimidine, piperidine, piperazine, morpholine, indole or quinoline ring.

A halo atom is, for example, a fluoro, chloro, bromo or iodo atom, preferably a chloro or a bromo atom.

The physiologically acceptable acid addition salts of the compounds of Formula I are the acid addition salts formed with physiologically acceptable inorganic acids, such as hydrochloric acid, sulfuric acid, etc., or with physiologically acceptable organic acids such as acetic acid, fumaric acid, lactic acid, etc.

A preferred subgroup of the compounds of Formula I consists of the hydroximic acid derivatives of Formula I wherein $R^1$ and $R^2$ together with the nitrogen atom to which they are attached for a piperidino group, $R^3$ is a pyridyl or a phenyl group and A represents a group of the formula b, wherein m and n have a value or 0. An especially preferred compound is the following: O-(3-piperidino-2-hydroxy-1-propyl)nicotinic amidoxime (Compound "A").

The compounds of Formula I can be prepared by the processes known from Hungarian Patent No. 177 578 and its equivalent U.S. Pat. No. 4,308,399.

The composition of the invention contains, in general 0.1 to 30% by mass, preferably 5 to 15% by mass, of a hydroximic acid derivative of Formula I or a physiologically acceptable acid addition salt thereof as the active ingredient and conventional carriers used in cosmetic formulations.

The composition of the invention can be used in conventional cosmetic formulations suitable for the topical treatment of the skin surface. Preferred formulations are creams, body emulsions, sun-emulsions, skin treatment foams, sprays, skin regenerating ampoules, etc.

The composition of the invention may contain, in addition to the active ingredient, the conventional carriers of cosmetic formulations generally in an amount of 70 to 99.9% by mass. Suitable carriers are, for example, one- or two-basic alcohols having a saturated or an unsaturated carbon chain, such as cetyl alcohol, stearyl alcohol, cetyl stearyl glycol, oleyl alcohol, lauryl alcohol, ethylene glycol, propylene glycol, glycerol; natural fats and oils, such as olive oil, avocado oil, wheat-germ oil, maize-germ oil, lanolin, cocoa-butter; higher hydrocarbons, such as VASELINE™ oil, VASELINE™ (petrolatum); beeswax; cellulose derivatives; emulsifiers, such as sodium lauryl sulfate, fatty acid or oleic acid esters of sorbitan, fatty acid or oleic acid esters of polyethylene glycols, sorbitan ethers of fatty alcohols or oleic alcohols, polyethylene glycol ethers of fatty alcohols or oleic alcohols, glycerides of fatty acids; vitamins, herb extracts such as chamomile extract; preservatives, such as methyl p-hydroxy-benzoate, chlorohexidine gluconate; light protecting factors, etc.

The composition of the invention is prepared by blending the ingredients thereof, in a manner known per se. In case of compositions based on a water/oil emulsion, in general, the ingredients of the fatty phase and those of the aqueous phase are separately admixed, then the two phases are blended using a fatty phase of elevated temperature, if required. The active ingredient of Formula I is added, preferably in an aqueous solution, to the fatty phase or to the mixture of the other ingredients.

The effect of the hydroximic acid derivatives of Formula I on photoaging was studied in the following tests.

1. Prevention of Photoaging of the Skin

The prevention of the photoaging of the skin was examined on 5 week old, nude mice of the origin CRL:CDI/nu-nu. On the skin surface of each animal, in the pectoral and abdominal regions, two uncovered squares of 1×1 cm were exposed to UV-B light, while the areas surrounding the test squares were covered to insure light protection. The two squares were also separated from each other by a covered square of 1 $cm^2$. The 1 $cm^2$ test areas were irradiated by UV-B light of 10.8 $J/cm^2$ intensity (corresponding to tenfold of the minimal erythema dose). In the abdominal region, the test square was irradiated without pretreatment, while the other test square (in the pectoral region) was pretreated with the composition of Example 7 containing 15% by mass of Compound "A". 20 hours after the irradiation, on the test square without pretreatment, a livid green skin color, as well as a bullous, necrotic cutaneous lesion could be observed that corresponds to a sunburn of category II/2 to III/1. In contrast, on the test square pretreated with the composition of the invention, no erythema could be observed. Compared with the control mice that were neither pretreated nor irradiated, no difference could be detected between the control animals and the animals pretreated with the composition of the invention, then irradiated.

The above experiment establishes that the skin surface is protected from the damaging effects of the UV-B light by the compounds of Formula I and the cosmetic composition of the invention, respectively, at a tenfold minimal erythema dose of UV. Thus, photoaging of the skin is effectively prevented when the skin surface is treated with the cosmetic composition of the invention before exposure to UV light.

2. Reduction of the Photoaging of the Skin

The photoaging inhibition effect of the compounds of Formula I was examined in guinea pigs. The skin surface of 8 guinea pigs was depilated, then on both sides of each animal, 1 $cm^2$ areas were irradiated by UV-B light of 100 $mJ/cm^2$ intensity. After the irradiation, one side of each animal was covered with the cream of Example 1 comprising 4% by mass of Compound "A" as the active ingredient.

The other side of each animal was covered with a mixture of cosmetic carriers comprising no active ingredient (i.e., a cream corresponding to that of Example 1 was used; however, said cream contained water instead of the active ingredient). Thus, an internal control was used in the experiment.

Four animals were treated with the cream immediately after the irradiation, then the treatment was repeated daily for a week (group I). The skin surface of the other four animals was irradiated, then treated with the cream of the invention and the control cream, respectively, with a single application 24 hours after the irradiation (group II).

In the animals of group I, minimal erythema could be observed on the skin surface irradiated and treated with the composition of the invention 24 and 48 hours after the irradiation. On the skin surface used as the control, an area without epithelium could be noticed, and this state persisted during the 7 days of observation. From the $4^{th}$ day, no difference could be detected between the skin surface irradiated and treated with the composition of the invention and the surrounding skin area.

In the animals of group II, on the treated area, as well as on the control area, skin injuries (vesicula, bulla) could be observed, then an area without epithelium developed. On the $7^{th}$ day after the irradiation, the area treated with the composition of the invention was epithelialized.

The above experiment establishes that the skin surface is protected from the damaging effects of the UV-B light by the composition of the invention and the compound of Formula I, respectively. If the skin surface is treated with the composition of the invention immediately after the irradiation, only mild injury of the epithelium is experienced. Thus, the photoaging processes of the skin are reduced.

Skin injuries developed by UV-B radiation are healed by treatment with the cosmetic composition of the invention in a shorter time than without treatment. The compound of Formula I exerts an epithelizing effect.

Thus, a further embodiment of the invention consists of a method for the prevention and/or reduction of the photoaging processes of skin, said method comprising applying to the affected skin surface a cosmetically effective, non-toxic amount of a hydroximic acid derivative of Formula I or a physiologically acceptable acid addition salt thereof and any necessary cosmetic carrier.

Suitably, the skin surface is treated with a cosmetic composition comprising 0.1 to 30%, preferably 5 to 15% by mass of a hydroximic acid derivative of Formula I or a physiologically acceptable acid addition salt thereof.

Preferably, the skin surface is treated with O-(3-piperidino-2-hydroxy-1-propyl)-nicotinic-amidoxime or a physiologically acceptable acid addition salt thereof.

In addition to photoaging, other skin conditions that can be treated or prevented with the composition of the invention are dry skin;

actinic keratosis, actinic prurigo (Lopez-Gonzalez's disease);

polymorphic light exanthema;

toxic photopathy;

photo-allergy;

purpura senilis;

solar atrophy of skin;

puberal strias (stria migrans);

elastoma diffusum (old skin);

X-ray dermatitis;

gouty polylchondritis;

decubitus ulcer (bedsore).

The invention is further elucidated by means of the following Formulation Examples.

EXAMPLE 1

Cream (Oil/Water)

The cream consists of the following ingredients:

| Compound A | 5.0% by mass |
|---|---|
| cetylstearyl alcohol | 7.5% by mass |
| stearic acid | 9.0% by mass |
| glycerol monostearate | 2.0% by mass |
| sodium lauryl sulfate | 0.5% by mass |
| methyl p-hydroxybenzoate | 0.1% by mass |
| distilled water | 75.9% by mass |
| | 100.0% by mass |

The lipophilic ingredients (cetylstearyl alcohol, stearic acid and glycerol monostearate) are melted over a water bath. The sodium lauryl sulfate and methyl p-hydroxybenzoate are dissolved in about 38 ml of distilled water at 60 to 65° C., the pH of the solution is adjusted by the addition of diluted aqueous sodium hydroxide solution to a value of 9 to 10, then the aqueous solution is admixed into the mixture of the lipophilic ingredients, and the emulsion obtained is stirred until cold. The active ingredient is dissolved in the remaining water, and the solution is admixed into the cooled cream.

EXAMPLE 2

Cream (Water/Oil)

The cream consists of the following ingredients:

| Compound A | 5.0% by mass |
|---|---|
| cetylstearyl alcohol | 12.0% by mass |
| white wax | 10.0% by mass |
| neutral oil | 35.0% by mass |
| Imwitor ® 780 K (partial glycerides of vegetable fatty acids) | 5.0% by mass |
| methyl p-hydroxybenzoate | 0.1% by mass |
| distilled water | 32.9% by mass |
| | 100.0% by mass |

The ingredients are blended using the method described in Example 1.

EXAMPLE 3

Cream (Water/Oil)

The cream consists of the following ingredients:

| Compound A | 5.0% by mass |
|---|---|
| cetylstearyl alcohol | 2.0% by mass |
| white wax | 1.5% by mass |
| lanalcol | 2.5% by mass |
| cholesterol | 1.0% by mass |
| white vaseline | 43.0% by mass |
| sodium tetraborate | 2.0% by mass |

| | |
|---|---|
| methyl p-hydroxybenzoate | 0.1% by mass |
| distilled water | 42.9% by mass |
| | 100.0% by mass |

The ingredients are blended using the method described in Example 1.

EXAMPLE 4

Moisturizing Cream for Night

The cream consisting of the following ingredients is prepared using the method described in Example 1:

| | |
|---|---|
| Compound A | 5.0% by mass |
| cetyl alcohol | 5.0% by mass |
| lanolin (anhydrous) | 5.0% by mass |
| cocoa-butter | 5.0% by mass |
| vaseline | 5.0% by mass |
| vaseline oil | 5.0% by mass |
| isopropyl myristate | 1.0% by mass |
| isopropyl palmitate | 1.0% by mass |
| wheat germ oil | 10.0% by mass |
| evening primrose oil | 5.0% by mass |
| vitamin A | 0.03% by mass |
| vitamin E | 0.05% by mass |
| glycerol | 5.0% by mass |
| propylene glycol | 5.0% by mass |
| methyl p-hydroxybenzoate | 0.2% by mass |
| perfume | 0.1% by mass |
| water, demineralized | 42.62% by mass |
| | 100.00% by mass |

EXAMPLE 5

Moisturizing Cream for Day

The cream consisting of the following ingredients is prepared by the method described in Example 1.

| | |
|---|---|
| Compound A | 5.0% by mass |
| cetyl alcohol | 5.0% by mass |
| lanolin (anhydrous) | 5.0% by mass |
| vaseline | 5.0% by mass |
| vaseline oil | 5.0% by mass |
| isopropyl myristate | 1.0% by mass |
| isopropyl palmitate | 1.0% by mass |
| borage oil | 4.0% by mass |
| peanut oil | 11.0% by mass |
| vitamin A | 0.03% by mass |
| vitamin E | 0.05% by mass |
| glycerol | 5.0% by mass |
| propylene glycol | 5.0% by mass |
| methyl p-hydroxybenzoate | 0.2% by mass |
| perfume | 0.1% by mass |
| water, demineralized | 47.62% by mass |
| | 100.00% by mass |

EXAMPLE 6

Body Milk

The body milk consisting of the following ingredients is prepared by the method described in Example 1.

| | |
|---|---|
| Compound A | 4.0% by mass |
| stearic acid monoglyceride | 2.0% by mass |
| cetylstearyl alcohol | 2.0% by mass |
| peanut oil | 5.0% by mass |
| vaseline oil | 3.0% by mass |
| polyoxyethylene cetylstearyl alcohol (degree of polymerization: 20) | 2.0% by mass |
| glycerol | 4.0% by mass |
| methyl p-hydroxybenzoate | 0.2% by mass |
| propyl p-hydroxybenzoate | 0.1% by mass |
| butylhydroxytoluene | 0.01% by mass |
| water, demineralized | 77.69% by mass |
| | 100.00% by mass |

EXAMPLE 7

Cream (Water/Oil)

The cream consists of the following ingredients:

| | |
|---|---|
| Compound A | 15.0% by mass |
| cetylstearyl alcohol | 10.0% by mass |
| white wax | 10.0% by mass |
| neutral oil | 30.0% by mass |
| Imwitor ® 780 K (partial glycerides of vegetable fatty acids) | 5.0% by mass |
| methyl p-hydroxybenzoate | 0.1% by mass |
| distilled water | 29.9% by mass |
| | 100.0% by mass |

The ingredients are blended using the method described in Example 1.

What is claimed is:

1. A composition comprising 0.1 to 30% by total mass of said composition of a hydroximic acid derivative of the formula

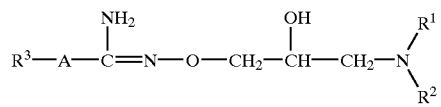

wherein $R^1$ is a hydrogen atom or a $C_{1-5}$ alkyl group;

$R^2$ is a hydrogen atom or a $C_{1-5}$ alkyl group, a $C_{3-8}$ cycloalkyl group or a phenyl group, optionally substituted by a hydroxy group or a phenyl group; or $R^1$ and $R^2$ together with the nitrogen atom to which they are attached form a 5 to 8 membered saturated or unsaturated ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of the formula $$—(CH)_{\overline{m}}—(CH)_{\overline{n}}—$$
$\quad\quad\;\;|\quad\quad\quad|$
$\quad\quad R^4\quad\quad R^5$ (a)

wherein $R^4$ is a hydrogen atom or a phenyl group;

$R^5$ is a hydrogen atom or a phenyl group;

m has a value of 0, 1 or 2; and n has a value of 0, 1 or 2;

or a physiologically acceptable acid addition salt thereof as the active ingredient and a carrier that is in the form of a cream, lotion, foam or spray.

2. The cosmetic composition of claim 1, wherein $R^1$ and $R^2$ together with the nitrogen atom to which they are attached form a piperidino group, $R^3$ is a pyridyl or a phenyl group, A represents a group of the formula a, $$—(CH)_{\overline{m}}—(CH)_{\overline{n}}—$$
$\quad\quad\;\;|\quad\quad\quad|$
$\quad\quad R^4\quad\quad R^5$ (a)

wherein $R^4$ is a hydrogen atom or a phenyl group;

$R^5$ is a hydrogen atom or a phenyl group;

and m and n have a value of 0.

3. The cosmetic composition of claim 1, wherein the compound of Formula I is O-(3-piperidino-2-hydroxy-1-propyl)nicotinic amidoxime.

4. The cosmetic composition of claim 1, wherein the active ingredient is present at 5 to 15% by mass of the composition.

5. The cosmetic composition of claim 2, wherein the active ingredient is present at 5 to 15% by mass of the composition.

6. The cosmetic composition of claim 3, wherein the active ingredient is present at 5 to 15% by mass of the composition.

7. A method for reducing the incidence of photoaging processes of the skin comprising applying to the affected skin surface an amount of the composition effective for reducing the incidence of photoaging processes of the skin said composition comprising a hydroximic acid derivative of the formula $$R^3—A—\underset{\underset{NH_2}{|}}{C}=N—O—CH_2—\underset{\underset{OH}{|}}{CH}—CH_2—N\overset{R^1}{\underset{R^2}{<}}$$

(I)

wherein $R^1$ is a hydrogen atom or a $C_{1-5}$ alkyl group;

$R^2$ is a hydrogen atom or a $C_{1-5}$ alkyl group, a $C_{3-8}$ cycloalkyl group or a phenyl group, optionally substituted by a hydroxy group or a phenyl group; or $R^1$ and $R^2$ together with the nitrogen atom to which they are attached form a 5 to 8 membered saturated or unsaturated ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of the formula $$—(CH)_{\overline{m}}—(CH)_{\overline{n}}—$$
$\quad\quad\;\;|\quad\quad\quad|$
$\quad\quad R^4\quad\quad R^5$ (a)

wherein $R^4$ is a hydrogen atom or a phenyl group;

$R^5$ is a hydrogen atom or a phenyl group;

m has a value of 0, 1 or 2; and n has a value of 0, 1 or 2; or a physiologically acceptable acid addition salt thereof as the active ingredient.

8. The method of claim 7, wherein in the compound of the formula (I) $R^1$ and $R^2$ together with the nitrogen atom to which they are attached form a piperidino group, $R^3$ is a pyridyl or a phenyl group, A represents a group of the formula a, $$—(CH)_{\overline{m}}—(CH)_{\overline{n}}—$$
$\quad\quad\;\;|\quad\quad\quad|$
$\quad\quad R^4\quad\quad R^5$ (a)

wherein $R^4$ is a hydrogen atom or a phenyl group;

$R^5$ is a hydrogen atom or a phenyl group;

and m and n have a value of 0.

9. The method of claim 7, wherein the compound of the formula (I) is O-(3-piperidino-2-hydroxy-1-propyl) nicotinic amidoxime.

10. The method of claim 7, wherein the active ingredient is present at 5 to 15% by mass of the composition.

11. The method of claim 8, wherein the active ingredient is present at 5 to 15% by mass of the composition.

12. The method of claim 9, wherein the active ingredient is present at 5 to 15% by mass of the composition.

13. A method for reducing the incidence of sunburn comprising administering to the skin of a subject an amount of a composition comprising O-(3-piperidino-2-hydroxy-1-propyl) nicotinic amidoxime in an amount effective to reduce the incidence of sunburn.

14. A method for reducing the incidence of photodamage by radiation with UV-B radiation comprising administering to the skin of a subject an amount of a composition effective to reduce the incidence of photodamage by UV-B radiation, said composition comprising a compound of the formula (I)

$$R^3—A—\underset{\underset{NH_2}{|}}{C}=N—O—CH_2—\underset{\underset{OH}{|}}{CH}—CH_2—N\overset{R^1}{\underset{R^2}{<}}$$

(I)

wherein $R^1$ is a hydrogen atom or a $C_{1-5}$ alkyl group;

$R^2$ is a hydrogen atom or a $C_{1-5}$ alkyl group, a $C_{3-8}$ cycloalkyl group or a phenyl group, optionally substituted by a hydroxy group or a phenyl group; or $R^1$ and $R^2$ together with the nitrogen atom to which they are attached form a 5 to 8 membered saturated or unsaturated ring that optionally comprises one or more further nitrogen or oxygen atoms, wherein said ring can be optionally condensed with a benzene ring;

$R^3$ is a hydrogen atom, a phenyl group, a naphthyl group or a pyridyl group wherein said groups can optionally be substituted by one or more halo atoms or $C_{1-4}$ alkoxy groups;

A is a group of the formula

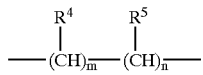

a wherein $R^4$ is a hydrogen atom or a phenyl group;

$R^5$ is a hydrogen atom or a phenyl group;

m has a value of 0, 1 or 2; and n has a value of 0, 1 or 2;

or a physiologically acceptable acid addition salt thereof as the active ingredient.

15. The method of claim 14, wherein in the compound of the formula (I) $R^1$ and $R^2$ together with the nitrogen atom to which they are attached form a piperidino group, $R^3$ is a pyridyl or a phenyl group, A represents a group of the formula a,

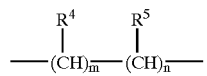

a wherein $R^4$ is a hydrogen atom or a phenyl group;

$R^5$ is a hydrogen atom or a phenyl group;

and m and n have a value of 0.

16. The method of claim 14, wherein the compound of the formula (I) is O-(3-piperidino-2-hydroxy-1-propyl) nicotinic amidoxime.

17. The composition of claim 1, wherein the carrier comprises a substance selected from the group consisting of natural fats, natural oils, cellulose derivatives, emulsifiers, fatty acid esters of polyethylene glycols, oleic acid esters of polyethylene glycols, sorbitan ethers of fatty alcohols, sorbitan ethers of oleic alcohols, polyethylene glycol ethers of fatty alcohols, polyethylene glycol ethers of oleic alcohols, glycerides of fatty acids and herb extracts.

18. The composition of claim 1, wherein the carrier comprises a substance selected from the group consisting of cetyl alcohol, stearyl alcohol, cetylstearyl alcohol, oleyl alcohol, lauryl alcohol, ethylene glycol, propylene glycol, glycerol, olive oil, avocado oil, wheat-germ oil, maize-germ oil, lanolin, cocoa-butter, petrolatum oil, petrolatum, beeswax, sodium lauryl sulfate, fatty acid esters of sorbitan and oleic acid esters of sorbitan.

* * * * *